(12) United States Patent
Drapeau et al.

(10) Patent No.: US 8,430,667 B2
(45) Date of Patent: Apr. 30, 2013

(54) REFLECTED GINGIVAL TISSUE RETRACTOR DEVICE FOR SURGICAL DENTAL PROCEDURES, KIT AND METHOD FOR USE THEREOF

(75) Inventors: Susan J. Drapeau, Cordova, TN (US); Kelly Brook Emerton, Memphis, TN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 13 days.

(21) Appl. No.: 13/019,429

(22) Filed: Feb. 2, 2011

(65) Prior Publication Data

US 2012/0196246 A1    Aug. 2, 2012

(51) Int. Cl.
    *A61C 5/12*    (2006.01)
(52) U.S. Cl.
    USPC ......................................................... 433/139
(58) Field of Classification Search .............. 433/37–44, 433/93–94, 136–140; D24/139, 176; 600/201, 600/206, 210, 215, 217–219, 222, 229, 235–242; 128/851, 869, 859
    See application file for complete search history.

(56) References Cited

U.S. PATENT DOCUMENTS

| | | | |
|---|---|---|---|
| 4,002,162 A * | 1/1977 | Weisser | 600/242 |
| 4,004,345 A * | 1/1977 | Ely | 433/139 |
| 4,733,354 A | 3/1988 | Potter et al. | |
| 4,854,867 A | 8/1989 | Meinershagen | |
| 5,022,859 A | 6/1991 | Oliva | |
| 5,609,485 A | 3/1997 | Bergman et al. | |
| 5,782,762 A | 7/1998 | Vining | |
| 5,899,694 A | 5/1999 | Summer | |
| 5,908,383 A | 6/1999 | Brynjestad | |
| 6,083,162 A | 7/2000 | Vining | |
| 6,272,366 B1 | 8/2001 | Vining | |
| 6,482,152 B2 * | 11/2002 | Kim | 600/210 |
| 6,575,749 B1 | 6/2003 | Greenwald | |
| 6,612,839 B2 | 9/2003 | Loynes | |
| 6,675,044 B2 | 1/2004 | Chen | |
| 6,694,163 B1 | 2/2004 | Vining | |
| 6,736,640 B1 * | 5/2004 | Ellenbecker | 433/93 |
| 6,882,271 B2 | 4/2005 | Hendrickson | |
| 6,909,913 B2 | 6/2005 | Vining | |
| 6,976,842 B1 | 12/2005 | Miggantz | |
| 6,994,548 B2 | 2/2006 | Perret, Jr. | |
| 7,153,134 B2 | 12/2006 | Coopersmith | |
| 7,209,578 B2 | 4/2007 | Saito et al. | |
| 7,241,143 B2 | 7/2007 | Discko, Jr. et al. | |

(Continued)

*Primary Examiner* — Cris L Rodriguez
*Assistant Examiner* — Matthew Seward
(74) *Attorney, Agent, or Firm* — Sorell Lenna & Schmidt LLP

(57) ABSTRACT

A gingival tissue retractor for retracting gingival tissue away from tooth and bone during a surgical procedure having an alveolar bone grip having an open frame structure positionable over at least one tooth and along a predetermined segment of an alveolar bone and providing an inward resilient force about opposite sides of the alveolar bone for maintaining position of the gingival retractor; a first gingival reflector having a solid plate structure and attached to a lower section of one side of the alveolar bone grip for providing a primarily downward force to gingival tissue on one side of the alveolar bone; and a second gingival reflector having a solid plate structure and attached to a lower section of another side of the alveolar bone grip for providing a primarily downward force to gingival tissue on another side of the alveolar bone.

16 Claims, 4 Drawing Sheets

U.S. PATENT DOCUMENTS

| | | |
|---|---|---|
| 7,577,573 B2 | 8/2009 | Janas, III et al. |
| 7,783,503 B2 | 8/2010 | Janas, III et al. |
| 7,792,565 B2 | 9/2010 | Vining |
| 2004/0209224 A1* | 10/2004 | Heasley ........................ 433/139 |

* cited by examiner

REFLECTED GINGIVAL TISSUE RETRACTOR DEVICE FOR SURGICAL DENTAL PROCEDURES, KIT AND METHOD FOR USE THEREOF

TECHNICAL FIELD

The present disclosure generally relates to a surgical device and more particularly to a reflected gingival tissue retractor device for surgical dental procedures, kit and a method for use thereof.

BACKGROUND

During all surgical dental procedures where gingival tissue is reflected away from the teeth and alveolar bone, there is a need to maintain the newly reflected gingival tissue away from the area of surgery. Gingival tissue is of great annoyance because it often gets injured, cut, and is in the way of the surgeon, thereby requiring additional assistance to hold the tissue back, while keeping out of the way of the surgical procedure.

SUMMARY OF THE INVENTION

Accordingly, a reflected gingival tissue retractor device for surgical dental procedures, kit and a method for use thereof are provided.

In one embodiment, in accordance with the principles of the present disclosure, a reflected gingival tissue retractor device for surgical dental procedures is provided. The device includes an alveolar bone grip having an open frame structure positionable over at least one tooth and along a predetermined segment of an alveolar bone and providing an inward resilient force about opposite sides of the alveolar bone for maintaining position of the gingival retractor; a first gingival reflector having a solid plate structure and attached to a rawer section of one side of the alveolar bone grip for providing a primarily downward force to gingival tissue on one side of the alveolar bone; and a second gingival reflector having a solid plate structure and attached to a lower section of another side of the alveolar bone grip for providing a primarily downward force to gingival tissue on another side of the alveolar bone.

In another embodiment, in accordance with the principles of the present disclosure, a reflected gingival tissue retractor device for surgical dental procedures is provided. The device includes an alveolar bone grip having an open frame structure positionable over at least one tooth and along a predetermined segment of an alveolar bone and providing an inward resilient force about opposite sides of the alveolar bone for maintaining position of the gingival retractor, comprising: a first and a second frame portion composed of a bent elastic material, each of said first and second frame portion, comprising: a central section of a primarily arched shape having a lower gripper portion resiliently biased inward by said arched shape, said elastic material providing an inward resilient force to said lower gripper portion; and a first and a second outer section each looped about itself near said gripper portion and extending outward from opposite sides of said central section, said loop providing a downward resilient force to said outer sections; a first gingival reflector having a plate-like structure connected between the first of the outer sections of each of the first and the second frame portion; a second gingival reflector having a plate-like structure connected between the second of the outer sections of each of the first and the second frame portion; and at least one cross member connected between said central section of said first and second frame portions.

In yet another embodiment, in accordance with the principles of the present disclosure, a method for using a reflected gingival tissue retractor device for surgical dental procedures is provided. The method includes applying a force to gingival reflectors of a gingival retractor in a primarily upward direction to elevate the gingival reflectors; applying further force to the gingival reflectors in a primarily inward direction to expand a grip portion of an open frame attached to said gingival reflectors; placing the gingival retractor in its operative position over at least one tooth, wherein a leading edge of the grip portion of the frame is introduced between retracted gingival tissue and alveolar bone; relaxing the force on the gingival reflectors to produce a gripping force by said grip portion about a predetermined length of said alveolar bone; and releasing said force from said gingival reflectors allowing the gingival reflectors to move to a primarily downward position that reflects the gingival tissue away from the alveolar bone, wherein said open frame provides an open operating environment about the at least one tooth and the alveolar bone.

In yet a further embodiment, in accordance with the principles of the present disclosure, a kit including a reflected gingival tissue retractor device for surgical dental procedures is provided. The kit includes a gingival retractor for retracting reflected gingival tissue; and a plurality of absorbent pads for insertion in said absorbent pad receptacles.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
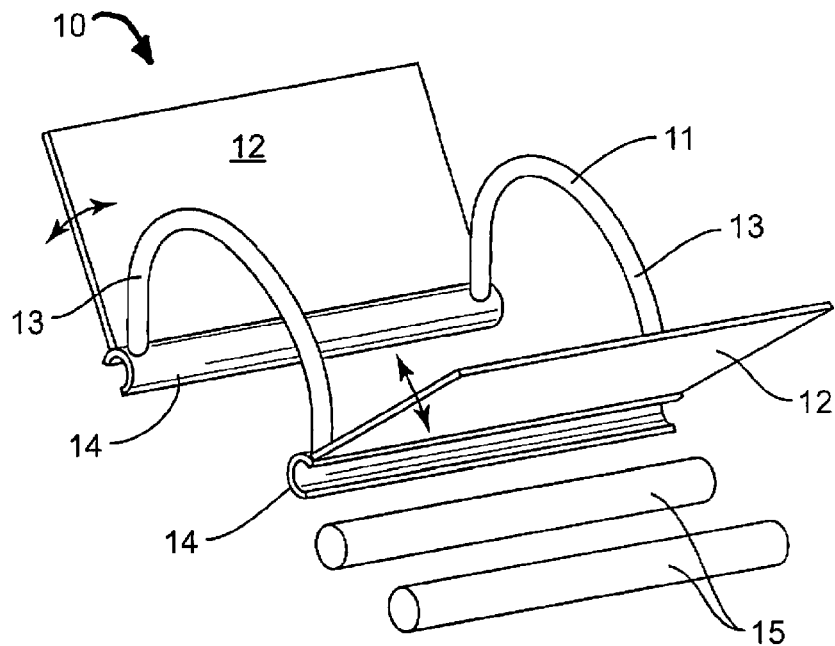
FIG. 1 is a perspective view of a reflected gingival retractor according to an embodiment of the present invention.

The exemplary embodiments of the reflected gingival retractor device for surgical dental procedures disclosed are discussed in terms of medical devices for dental applications for retracting gingival tissue during a surgical dental procedure.

It is envisioned that the reflected gingival tissue retractor device disclosed provides a reliable and safe access to a dental region to perform dental surgery. It is further envisioned that the reflected gingival retractor device is configured to maintain a gingival flap in a retracted position during a surgical procedure, and can include a removable absorbent pad to 'sop up' pooled blood during the procedure. The gingival retractor is easily removed, and can be adjusted to fit different size mouths.

The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a gingival retractor in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of a reflected gingival retractor 10/30 in accordance with the principles of the present disclosure.

Dental procedures are required in many dental conditions. Some of these conditions can include tooth extractions, dental disease, dentures or bridgework, trauma, misalignment, tumors, osteomyelitis, osteoradionecrosis, and developmental deformities. During dental procedures to address and/or correct these conditions, a surgeon often requires access to the alveolar bone in either the mandible or maxilla. In order for this access to be obtained, the surgeon may be required to reflect gingival tissue away from a tooth and the underlying alveolar bone. A gingival retractor can be used to reflect the gingival tissue away from the tooth and alveolar bone.

Typical gingival retractors are hand-held devices that can consist of a rigid handle and head, the head being shaped such that it can be inserted between a tooth and the gingival tissue and when a force is applied to the handle, the gingival tissue can be reflected away from the tooth and the alveolar bone. In order to maintain retraction of the reflected gingival tissue continued force is required on the gingival retractor. This continued force must be applied by the surgeon, leaving only one hand for other surgical procedures, or by an assistant, thus crowding the confined surgical area.

FIG. 1 is a perspective view of a reflected gingival retractor 10 according to an embodiment of the present invention. Gingival retractor 10 can include a frame (or alveolar bone clip) 11 and gingival reflectors 12. Frame 11 can be comprised of two upper sections 13 of bent elastic material connected and spaced apart by two frame legs 14. The gingival reflectors 12 can be comprised of a semi-rigid solid material. A lower length of a gingival reflector 12 is connected to a frame leg 14; the other gingival reflector 12 is connected in a similar manner to the other frame leg 14. Although the gingival retractor 10 is described as being composed of distinct parts, the gingival retractor 10 can be manufactured as a single element through, for example, an injection molding process; other processes of manufacture are contemplated. As shown in FIG. 1, gingival retractor 10 provides an open operating space between the two upper sections 13 and between the two frame legs 14.

Each frame leg 14 can be configured to accommodate an absorbent pad 15 on the bottom thereof and used to sop up blood that accumulates during the surgical procedure. To achieve this, the frame leg 14 can have a concave shape at its bottom portion forming an absorbent pad receptacle to mate with the absorbent pad 15. The absorbent pad 15 can have a length approximately equal to the length of the frame leg 14.

Figure 2:
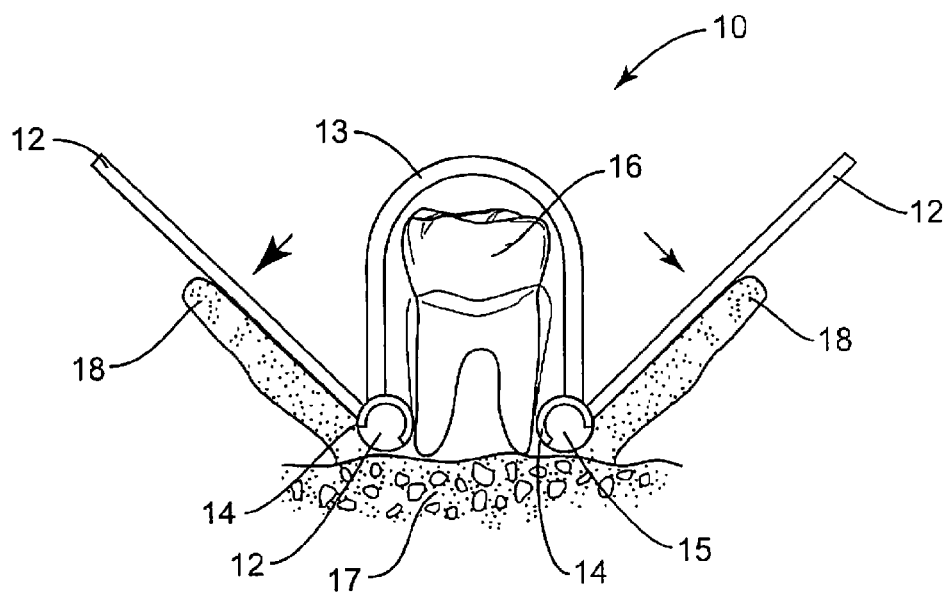
FIG. 2 is a cross section view of a reflected gingival retractor according to an embodiment of the present invention.

FIG. 2 is a cross section view of a reflected gingival retractor 10 according to an embodiment of the present invention. Gingival retractor 10 is shown in place about a tooth 16 and the alveolar bone 17. Gingival tissue 18 is show in a retracted state being reflected by gingival reflectors 12. Absorbent pads 15 are shown attached to the frame legs 14 and inserted between the alveolar bone 17 and the gingival tissue 18.

In operation the gingival retractor 10 has a relaxed position and a compressed position. In its relaxed position, the space between the two frame legs 14 should be less than the width of the alveolar bone 17 to which the gingival retractor 10 is to be attached and of such elasticity such that the gingival retractor 10 can be "clipped to" the alveolar bone 17 as shown in FIG. 2. By providing an inward force to the top edges of the gingival reflectors 12 tension is created in the upper sections 13 and the space between frame legs 14 is increased. The force required can be created by a pinching motion created between a thumb and forefinger. With continued force being applied, the gingival retractor 10 is moved into place over the tooth 16 and alveolar bone 17 and inserted between the gingival tissue 18 and the alveolar bone 17. As the force is relaxed, frame legs 14 compress about a predetermined length of the alveolar bone 17 due to the compression tension created by upper sections 13 attempting to return to their relaxed position. In order to provide sufficient operating space, the length of the frame legs 14 can be at least that of the length of a tooth 16 measured alone the alveolar bone 17. The gingival retractor 10 can be manufactured in different lengths to accommodate one or more teeth as desired. When the dental procedure is completed, inward force is again applied to the upper ends of the gingival reflectors 12 easing the force of the frame legs 14 about the alveolar bone 17 to allow easy removal of the gingival retractor 10.

Figure 3:
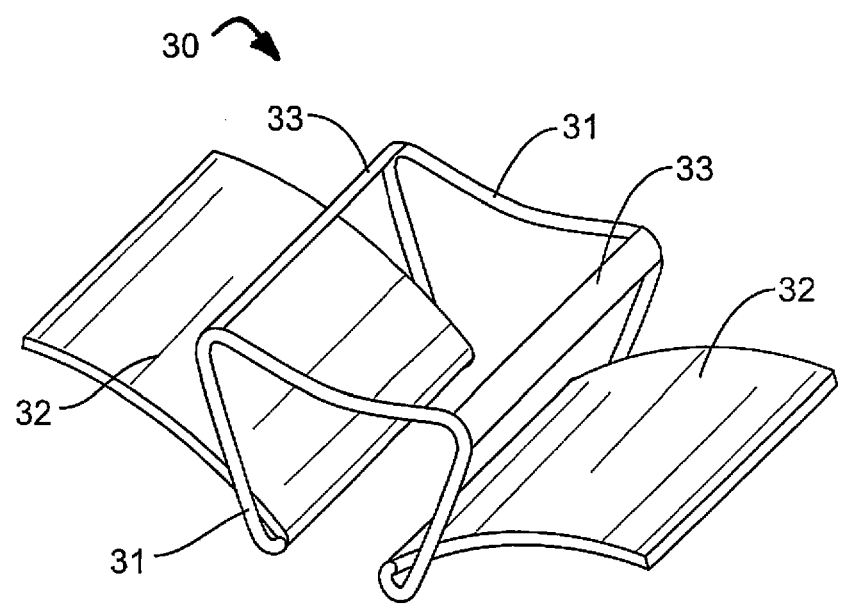
FIG. 3 is a perspective view of a reflected gingival retractor according to another embodiment of the present invention.
Figure 4A:
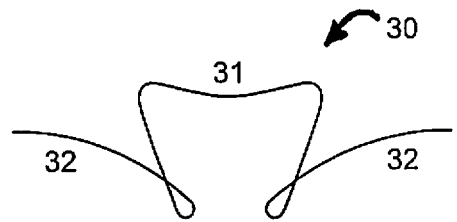
FIG. 4 is a diagram illustrating a method of using a reflected gingival retractor according to an embodiment of the present invention.
Figure 4B:
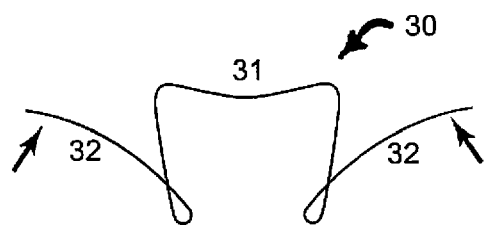
Figure 4C:
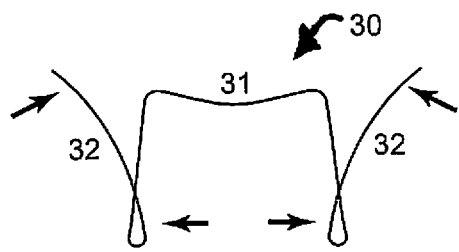
Figure 4D:
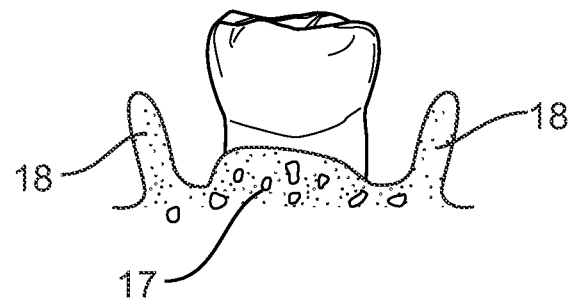
Figure 4D:
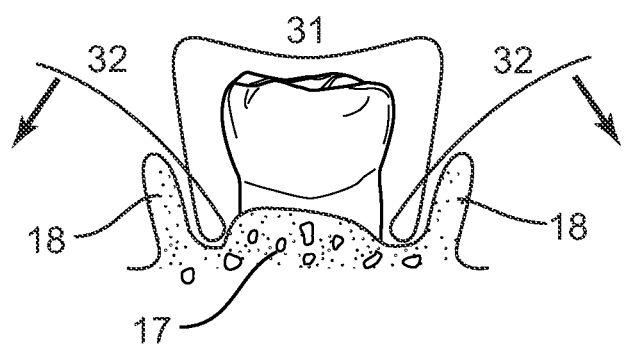
Figure 4E:
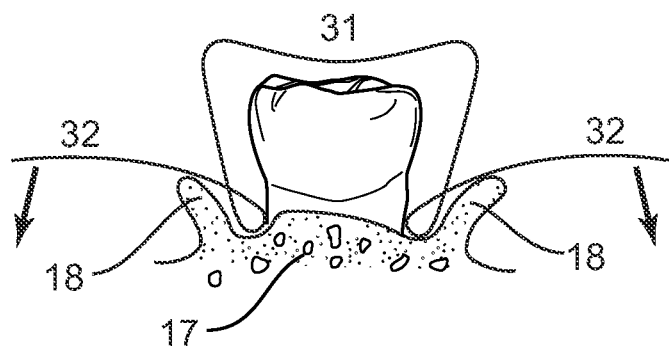

FIG. 3 is a perspective view of a reflected gingival retractor according to another embodiment of the present invention. As shown in FIG. 3, gingival retractor 30 is shown manufactured as a bent frame structure. In this embodiment, an upper section 31 and a first side edge of the gingival reflectors 32 comprise a first single structure of bent elastic spring material. Another upper section 31 and a second side edge of the gingival reflectors 32 comprise a second single structure of bent elastic spring material. Between the first and second single structure of bent elastic spring material made of semi-rigid solid material are gingival reflectors 32. Additional support members 33 can also be included to provide additional lateral support to the gingival retractor 30. Although not shown in FIG. 3, and in a similar manner as shown in FIGS. 1 and 2, absorbent pad receptacles can be provided along the position where the upper sections 31 meet with the gingival reflectors 32.

Although two structures are illustrated in the drawing as examples of the gingival retractor, various other shapes and sizes of the device are contemplated. By providing an alveolar bone clip having an open frame structure with gingival retractors connected thereto and capable of providing a downward force to gingival tissue when in place, the present invention can be realized.

FIG. 4 is a diagram illustrating a method of using a reflected gingival retractor according to an embodiment of the present invention. Diagram (a) illustrates the gingival retractor 30 in its pre-operative and relaxed position. Diagram (b) illustrates a force being applied to the gingival reflectors 32 in the direction of the arrows to elevate the gingival reflectors 32 and place them in contact with the frame 31. Diagram (c) illustrates continued force being applied to the gingival reflectors 32 to further elevate the gingival reflectors 32 and open the grip portion of the frame 31. Also illustrated in diagram (c) are tooth 16, alveolar bone 17 and gingival tissue 18, which is in its retracted but not fully reflected position. Diagram (d) illustrates the gingival retractor 30 being placed in its operative position wherein a leading edge of the grip portion of the frame 31 is introduced between the retracted gingival tissue 18 and the alveolar bone 17; as force on the gingival reflectors 32 is released, the grip portion of the frame 31 compresses about and engages, or "clips" onto, the alveolar bone 17. Diagram (e) illustrates force being removed from the gingival reflectors 32 allowing the gingival reflectors 32 to move to a position that reflects the gingival tissue 18 away from the alveolar bone 17, thus providing an open and free operating environment about the tooth 16 and alveolar bone 17. The gingival retractor 30 is removed by reversing the process.

In one embodiment, a gingival retractor as well as absorbent pads may be packaged as a system or kit. In such an embodiment, the kit may include a several sizes of gingival retractors and/or a plurality of absorbent pads, and other materials for treatment.

It is contemplated that the reflected gingival retractor can be used and manipulated by the surgeon using a single hand and when placed into position leaving both hands of the surgeon free.

The components of reflected gingival retractor can be fabricated from materials suitable for medical applications, including metals, polymers, ceramics, biocompatible materials, tissues, and/or their composites, depending on the particular application and/or preference of a medical practitioner. For example, the components of the reflected gingival retractor, individually or collectively, and which may be monolithically formed or integrally connected, can be fabricated from materials such as stainless steel, stainless steel alloys, titanium alloys, super-elastic titanium alloys, cobalt-chrome alloys, shape memory materials, such as super-elastic metallic alloys (e.g., Nitinol, super-elastic plastic metals, such as GINGIVAL METAL® manufactured by Toyotsu Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, and epoxy. Various components of the reflected gingival retractor may have material composites, including the above materials, to achieve various desired characteristics such as strength, rigidity, elasticity, compliance, degradability, biomechanical performance, durability and radiolucency or imaging preference. Components alternatively could be prepared from allogeneic or xenogeneic tissues, tissue composites, or biomaterial/tissue composites.

It is contemplated that the reflected gingival retractor may include therapeutic antibiotics, polynucleotides or polypeptides, which can be packed or otherwise disposed on or within the tacks. It is further contemplated that the reflected gingival retractor may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within a patient. Suitable biologically active agents include, for example, bone morphogenic protein (BMP), Growth and Differentiation Factors proteins (GDF) and cytokines.

One or all of the components of the gingival retractor may include one or a plurality of agents that can be configured as drug depots with medication for pain and may include antibiotics and/or therapeutics. It is envisioned that the agents may contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide tetracyclines, trimethoprim, trimethoprim-sulfamthoxazole and vancomycin.

The agent may also include immunosuppressives agents, such as, for example, steroids, cyclosporine, cyclosporine analogs, cyclophosphamide, methylprednisone, prednisone, azathioprine; FK-506; 15-deoxyspergualin; prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A dental device comprising:
   a retractor for retracting tissue comprising an alveolar bone clip having an open frame structure having a first arched frame component and a second arched frame component, said first and second frame components configured so that said retractor is positionable over at least one tooth and along a predetermined segment of an alveolar bone and so as to provide an inward resilient force about opposite sides of the alveolar bone for maintaining position of the retractor;

a first reflector having a solid plate structure attached to a lower section of one side of the alveolar bone clip for providing a primarily downward force to tissue on one side of the alveolar bone; a second reflector having a solid plate structure attached to a lower section of another side of the alveolar bone clip for providing a primarily downward force to tissue on another side of the alveolar bone;

a first absorbent pad receptacle positioned along said first reflector and attached to the lower section of the one side of the alveolar bone clip; and a second absorbent pad receptacle positioned along said second reflector and attached to the lower section of the other side of the alveolar bone clip, wherein a top edge of the first reflector and a top edge of the second reflector extend beyond a top of a central portion of the first and second arched frame components.

2. The dental device of claim 1, wherein the alveolar bone clip comprises:

the first arched frame component composed of an elastic material providing a first inward resilient force about ends of said first arched frame component;

the second arched frame component composed of an elastic material providing a second inward resilient force about ends of said second arched frame component;

a first frame leg attached to one end of each of the first and second arched frame components, and a second frame leg attached to another end of each of the first and second arched frame components;

wherein one edge of said first reflector is attached along said first frame leg and extends upward from said first frame leg and outward from said first and second arched frame components, and wherein one edge of said second reflector is attached along said second frame leg and extends upward from said second frame leg and outward from said first and second arched frame components.

3. The dental device of claim 2, configured so that when the first and second inward forces are applied to outer ends of said reflectors, said reflectors compress inward and a distance between said frame legs increases in a direction opposite to the inward resilient force about the ends of said arched frames.

4. The dental device of claim 2, wherein a length of the frame legs is greater than a width of a tooth along the alveolar bone.

5. The dental device of claim 2, wherein a height of said an alveolar bone clip is such that when the retractor is positioned along the predetermined segment of the alveolar bone the top of said arched frame components is configured to be placed above a top surface of said at least one tooth.

6. A retractor for retracting reflected gingival tissue, comprising:

an alveolar bone clip having an open frame structure positionable over at least one tooth and along a predetermined segment of an alveolar bone and providing an inward resilient force about opposite sides of the alveolar bone for maintaining position of the retractor, comprising:

a first and a second frame portion composed of a bent elastic material, each of said first and second frame portion comprising:

an upper section having an outer end;

a central section of a primarily arched shape having a lower gripper portion resiliently biased inward by said arched shape, said elastic material providing the inward resilient force to said lower gripper portion; and a first and second outer section each looped about itself adjacent to said gripper portion and extending outward from opposite sides of said central section, said loop providing a downward resilient force to said outer sections;

a first reflector having a plate-like structure connected between the first of the outer sections of each of the first and the second frame portion;

a second reflector having a plate-like structure connected between the second of the outer sections of each of the first and the second frame portion;

a first absorbent pad receptacle positioned along a bottom edge of said first reflector adjacent said loop; and a second absorbent pad receptacle positioned along a bottom edge of said second reflector adjacent said loop; and at least one cross member connected between said central section of said first and second frame portions, wherein a top edge of the first reflector and a top edge of the second reflector extend beyond a top of a central portion of the first and second frame portions.

7. The retractor of claim 6, configured so that when the inward force is applied to outer ends of said first and second reflectors said first and second reflectors compress inward and said distance between said loops legs increases in a direction opposite to the inward resilient force at the gripper portion.

8. The retractor of claim 6, wherein a length of the reflector is greater than a width of a tooth along the alveolar bone.

9. The retractor of claim 6, wherein a height of said alveolar bone clip is such that when the retractor is positioned along the predetermined segment of the alveolar bone the top of said central portion is above a top surface of said at least one tooth.

10. A method for retracting tissue, comprising:

attaching a first absorbent pad at a first grip portion of a frame of a retractor and a second absorbent pad to second grip portion of the frame;

applying a force to an upper edge of a first reflector and an upper edge of a second reflector of the retractor in a primarily upward direction to elevate the reflectors to form an open position of the frame, the upper edge of the first reflector and the upper edge of the second reflector extending beyond a top of a central portion of the frame of the retractor;

placing the retractor in an operative position over an at least one tooth, wherein a first leading edge of the first grip portion and the second leading edge of a second grip portion of the frame is introduced between a retracted gingival tissue and an alveolar bone;

relaxing the force on the reflectors to produce a gripping force by said grip portion about a predetermined length of said alveolar bone; and releasing said force from said reflectors allowing the reflectors to move to a primarily downward position that reflects the tissue away from the alveolar bone, wherein said open position of the frame provides an open operating environment about the at least one tooth and the alveolar bone.

11. The method for retracting tissue of claim 10, wherein said reflectors apply a downward force to the gingival tissue around said at least one tooth.

12. A kit for retracting gingival tissue, comprising:
   the retractor for retracting reflected tissue of claim 1; and
   a plurality of absorbent pads for insertion in said absorbent pad receptacles.

13. The kit for retracting gingival tissue of claim 12, wherein said retractor and said plurality of absorbent pads are disposable.

14. The kit for retracting tissue of claim 12, wherein said retractor and said plurality of absorbent pads are in a sterilized package.

15. The kit for retracting tissue of claim 12, wherein said complete kit is sterilized.

16. A kit for retracting gingival tissue, comprising:
   a plurality of retractors for retracting reflected tissue of claim 1, said plurality of retractors including retractors of varying lengths.

* * * * *